United States Patent
Xiao et al.

(10) Patent No.: US 11,684,239 B2
(45) Date of Patent: Jun. 27, 2023

(54) METHOD, SYSTEM AND COMPUTER READABLE MEDIUM FOR EVALUATING COLONOSCOPY PERFORMANCE

(71) Applicant: Chengdu Wision Medical Device Co., Ltd., Chengdu (CN)

(72) Inventors: Xiao Xiao, Chengdu (CN); Jingjia Liu, Chengdu (CN)

(73) Assignee: CHENGDU WISION MEDICAL DEVICE CO., LTD., Chengdu (CN)

(*) Notice: Subject to any disclaimer, the term of this patent is extended or adjusted under 35 U.S.C. 154(b) by 371 days.

(21) Appl. No.: 17/189,321

(22) Filed: Mar. 2, 2021

(65) Prior Publication Data

US 2022/0202275 A1   Jun. 30, 2022

(30) Foreign Application Priority Data

Dec. 29, 2020   (CN) ................ 202011605719.X

(51) Int. Cl.
| | | |
|---|---|---|
| *G06K 9/00* | (2022.01) | |
| *A61K 35/12* | (2015.01) | |
| *A61B 1/00* | (2006.01) | |
| *A61B 1/31* | (2006.01) | |

(Continued)

(52) U.S. Cl.
CPC ........ *A61B 1/00009* (2013.01); *A61B 1/0005* (2013.01); *A61B 1/31* (2013.01); *G06T 7/0012* (2013.01); *G16H 40/20* (2018.01); *G06T 2207/30028* (2013.01); *G06T 2207/30168* (2013.01)

(58) Field of Classification Search
CPC ............. G06K 9/00; A61K 35/12; A61B 1/00
USPC ....... 382/100, 103, 106, 128–133, 168, 199, 382/224, 254, 276, 286–291, 312; 600/339, 340
See application file for complete search history.

(56) References Cited

U.S. PATENT DOCUMENTS

| | | | |
|---|---|---|---|
| 7,738,683 B2 * | 6/2010 | Cahill | ................ G06T 7/0012 |
| | | | 382/128 |
| 9,392,961 B2 * | 7/2016 | Kimchy | ................ A61B 5/073 |

(Continued)

FOREIGN PATENT DOCUMENTS

CN   111861049 A   10/2020

*Primary Examiner* — Seyed H Azarian
(74) *Attorney, Agent, or Firm* — Chieh-Mei Wang

(57) ABSTRACT

A computer-implemented method for evaluating colonoscopy performance includes: (S1) splitting a video acquired during a colonoscopy examination into a plurality of colonoscopy images; (S2) assigning each of the colonoscopy images into a fold-inspection group or a non-fold-inspection group according to a first classification criterion and a second classification criterion, wherein the first classification criterion comprises at least one of clarity, exposure, level of tissue wrinkling, and level of occlusion in each of the colonoscopy images; and the second classification criterion comprises at least one of an amount of haustrum, an amount of colonic lumen, and a position of the colonic lumen in each of the colonoscopy images; and (S3) determining a performance rating of the colonoscopy examination according to an elapsed time of the fold-inspection group. The method classifies colonoscopy images more accurately and reliably, thereby providing an effective tool for quality assessment and guidance of colonoscopy examinations.

15 Claims, 8 Drawing Sheets

(51) Int. Cl.
    *G06T 7/00*     (2017.01)
    *G16H 40/20*     (2018.01)

(56) References Cited

U.S. PATENT DOCUMENTS

| | | | |
|---|---|---|---|
| 2007/0036402 A1* | 2/2007 | Cahill | G06T 7/0012 382/128 |
| 2010/0183210 A1* | 7/2010 | Van Uitert | G06T 7/0012 382/131 |
| 2017/0265747 A1* | 9/2017 | Tajbakhsh | G06T 7/0012 |

* cited by examiner

METHOD, SYSTEM AND COMPUTER READABLE MEDIUM FOR EVALUATING COLONOSCOPY PERFORMANCE

CROSS-REFERENCE TO RELATED APPLICATION

This application claims the priority under 35 U.S.C. § 119 of Chinese Application No. 202011605719.X, filed Dec. 29, 2020, the entirety of which is incorporated herein by reference.

FIELD OF THE INVENTION

The present disclosure relates to intelligent medical diagnostics, and more particularly to a computer-implemented method, an artificial intelligent system and a computer readable medium for evaluating colonoscopy performance.

BACKGROUND OF THE INVENTION

Colorectal cancer, developed from adenomatous polyps in precancerous lesion or early cancer, is highly malignant. An effective approach for prevention of colorectal cancer and reduction of its risk of death has been to screen, detect and remove adenomatous polyps at an early stage.

Colonoscopy is a standard procedure for colorectal cancer screening, and includes forward-viewing and withdrawal colonoscopy examinations. Quality of colonoscopy examinations is a primary factor influencing the resulting adenoma detection rate (ADR) and adenoma per colonoscopy (APC).

At present, there is no rational scientific method or standard for evaluating the quality of colonoscopy examinations. Total time for colonoscopy withdrawal has been used as the main reference for quality evaluation. For example, CN 111,861,049A discloses an image-based quality assessment and scoring system for colonoscopy examinations, in which requirements for assessing the quality of spiral colonoscopy are provided. Such requirements include: total withdrawal time, valid withdrawal time, amount of suspicious colonic segments observed, total time of examination, amount of screenshots, clarity of images, whether the ileocecal valve was reached, whether rectal retroflexion was performed, and completion and safety of examination. Accordingly, the quality of each spiral colonoscopy examination may be quantitated based on completion of each of the requirements.

However, the inventors found that, although widely used in the field, spiral colonoscopy is not accurate in lesion detection. For example, experienced physicians can fully expose and inspect the colonic mucosa, thus achieving high ADR and APC, without using the spiral withdrawal technique. Furthermore, it is common that the majority of colonoscopy images taken during withdrawal contain invalid views of the colonic mucosa; therefore, the total withdrawal time cannot reflect the quality of the colonoscopy. That is, longer withdrawal time does not equate higher ADR and APC of the physician. Therefore, referencing the total withdrawal time or other conventional requirements for quality evaluation of colonoscopy not only fails to accurately measure the performance of the physician, but also tends to mislead the physician into blindly aiming at fulfilling certain requirements without focusing on the examination itself, therefore resulting in poor performance and low ADR/APC of the colonoscopy.

BRIEF SUMMARY OF THE INVENTION

One object of the present disclosure is to provide an accurate and reliable model for evaluating colonoscopy performance. The model involves identification of colonoscopy images showing valid views of the colonic mucosa, by assigning each of the acquired colonoscopy images into a fold-inspection or non-fold inspection group according to a classification algorithm that includes criteria such as whether haustrum or colonic lumen is shown in the image, amount of haustrum shown, and position of colonic lumen in the image. After all valid colonoscopy images are identified, a performance rating of the colonoscopy examination may be determined according to the elapsed time of the fold-inspection group or the ratio of the elapsed time of the fold-inspection group over the total duration of the colonoscopy examination. Each of the acquired colonoscopy images may also be updated by addition of a marking for identifying the group to which the image is assigned, so as to guide the physician in real time during his/her colonoscopy operation. The classification algorithm is demonstrated to effectively screen out valid colonoscopy images that are in high positive correlation with ADR and APC. Consequently, the present disclosure breaks the conventional limits on quality assessment of colonoscopy examinations, and improves the technical field of medical diagnostics by providing a more accurate and reliable approach for evaluating and guiding colonoscopy operations.

The above object is achieved by the following technical solutions:

A computer-implemented method for evaluating colonoscopy performance is provided. The method includes the steps of:

(S1) splitting a video acquired during a colonoscopy examination into a plurality of colonoscopy images;

(S2) assigning each of the colonoscopy images into a fold-inspection group or a non-fold-inspection group according to a first classification criterion and a second classification criterion, wherein the first classification criterion includes at least one of clarity, exposure, level of tissue wrinkling, and level of occlusion in each of the colonoscopy images; and the second classification criterion includes at least one of an amount of haustrum, an amount of colonic lumen, and a position of the colonic lumen in each of the colonoscopy images; and (S3) determining a performance rating of the colonoscopy examination according to an elapsed time of the fold-inspection group.

In the present technical solution, the method uses the elapsed time of valid colonoscopy views as the reference parameter for quality evaluation. The longer the time of valid colonoscopy views had elapsed, the fuller the colonic mucosa was inspected, therefore suggesting higher colonoscopy quality.

Specifically, in Step (S1), the video acquired during a colonoscopy examination is first split into a plurality of static colonoscopy images. The video may be acquired during the forward-viewing process and/or the withdrawal process. For example, the physician may record the entire colonoscopy procedure in which the colonoscope is moved toward the ileocecal valve and withdrawn after the ileocecal valve is reached. In one or more embodiments, the video may be a real-time video and, after image classification, be added with markings in real time during the colonoscopy examination to instantly inform the physician of information such as the type of current view and the elapsed time of the fold-inspection group. In one or more embodiments, the video may also be a recorded video containing images of the entire colonoscopy examination. The video may be split frame by frame into a plurality of static colonoscopy images;

given that the length of time per frame is known, the elapsed time of each assigned group may be obtained.

Next, in Step (S2), each of the plurality of colonoscopy images is assigned into one of a plurality of groups according to a first classification criterion and a second classification criterion. The images meeting the requirements defined in the first and second criteria are assigned into the corresponding groups, each of which corresponds to one type of image view.

In the present technical solution, the first classification criterion includes at least one of clarity, exposure, level of tissue wrinkling, and level of occlusion in each of the colonoscopy images. During colonoscopy examinations, fast motion of the colonoscope, close proximity between the colonoscope and the colonic wall, foreign objects in the colon and the like may cause the colonoscopy images to blur, overexposed, or occluded, making it difficult to inspect the colonic mucosa or polyps on the colonic wall. These types of colonoscopy images, as the inventors verified, are negatively correlated with ADR and APC. Thus, these types of colonoscopy images are defined as invalid views and assigned into an inadequate-view group (a member of the non-fold-inspection group). The elapsed time of the inadequate-view group is considered invalid inspection time, therefore high percentage of time of the inadequate-view group over the entire examination represents poor colonoscopy performance.

The second classification criterion includes at least one of an amount of haustrum, an amount of colonic lumen, and a position of the colonic lumen in each of the colonoscopy images. The amount of colonic lumen refers to the amount of the colonic lumen observable in the colonoscopy image, and is thus either 0 or 1; the position of the colonic lumen is defined with respect to the central area of the colonoscopy image; and a haustrum is counted if the area between two adjacent semilunar folds is visible.

The colonoscopy images that are not assigned into the inadequate-view group are all assigned into the adequate-view group. Images in the adequate-view group contain clear views of exposed colonic mucosa, which facilitates inspection of the colonic mucosa and thus improves ADR and APC of the physician. Further, the colonoscopy images in the adequate-view group that meet the requirements defined in the second classification criterion are assigned into the fold-inspection group; whereas those not meeting the same requirements are assigned into a lumen-inspection group (another member of the non-fold-inspection group). As the inventors verified, the images in the fold-inspection group are highly positively correlated with ADR and APC; whereas the images in the lumen-inspection group have no statistically significant correlation with ADR or APC. For example, images in the adequate-view group that show the colonic wall but in absence of any haustrum or colonic lumen are positively correlated with ADR and APC; and those showing the colonic wall, the haustrum and the colonic lumen, but having the colonic lumen locating inside of the central area of the image, has no correlation with ADR or APC.

Finally, in Step (S3), once the colonoscopy images qualified for the fold-inspection group is screened out, the elapsed time of the fold-inspection group may be calculated, by for example multiplying the amount of images in the fold-inspection group by the length of time per image, to assess the quality of the colonoscopy performance. In one or more embodiments, the elapsed time of the fold-inspection group is used as the parameter for quality assessment. In one or more embodiments, the ratio of the elapsed time of the fold-inspection group over the total duration of colonoscopy examination is used as the evaluation parameter. In one or more embodiments, the ratio of the elapsed time of the fold-inspection group over the total duration of colonoscope withdrawal is used as the evaluation parameter.

The rationale behind the present technical solution is that since how colonoscopy examination is performed varies from one physician to another, the elapsed time of the fold-inspection group and the non-fold-inspection group would vary as well; moreover, the correlation between the fold-inspection group and ADR/APC, the key factors for assessing colonoscopy performance, is demonstrated to be much higher than that between the non-fold-inspection group and ADR/APC. Therefore, the elapsed time of the fold-inspection group represents a parameter with improved accuracy for evaluating the colonoscopy performance of the physician.

The evaluation method provided in the present disclosure uses the elapsed time of the fold-inspection group as the evaluation parameter to establish a scientific and reliable standard for quality assessment of colonoscopy performance. The method is also an effective tool for guiding physicians to adjust his/her colonoscopy operation real-time so as to increase the time for collecting images qualified for the fold-inspection group, therefore improving the quality of the colonoscopy examination. Meanwhile, the method would free physicians from having to comply with conventional requirements associated with spiral colonoscopy, and encourage them to focus on acquiring more valid images within a shorter amount of examination time, which would help reduce discomfort of the examinee as well.

In the present technical solution, the first classification criterion and the second classification criterion can be used simultaneously or sequentially. In a preferred embodiment of the classification method according to the present disclosure, the first classification criterion is used before the second classification criterion. Specifically, the step of (S2) may include: (S21) assigning each of the colonoscopy images into an inadequate-view group or an adequate-view group according to the first classification criterion; and (S22) assigning each image in the adequate-view group into the fold-inspection group or a lumen-inspection group according to the second classification criterion. The step of (S3) may include: determining the performance rating of the colonoscopy examination according to an elapsed time of at least one of the fold-inspection group, the lumen-inspection group, and the inadequate-view group.

In other embodiments, the second classification criterion may be used first to classify each colonoscopy image into either a preliminary fold-inspection group or a preliminary lumen-inspection group; the first classification criterion may then be used for classifying the images in the preliminary fold-inspection group into the fold-inspection group or the inadequate-view group, and for classifying the images in the preliminary lumen-inspection group into the lumen-inspection group or the inadequate-view group.

The classification method provided in the present technical solution adopts the principle of exclusion. First, the first classification criterion, which includes clarity, exposure, level of tissue wrinkling, and/or level of occlusion in each image, is used to screen out invalid colonoscopy images qualified for the inadequate-view group. The other images are assigned into the adequate-view group. Features of the images in the inadequate-view group may include: more than half of the total area of the image being so blurred, overexposed, or occluded that the colonic wall, the haustrum or the colonic lumen is hard to inspect.

Subsequently, the second classification criterion, which includes the amount of haustrum, the amount of colonic lumen, and the position of the colonic lumen in each image, is used to screen out images qualified for the fold-inspection group from those in the adequate-view group. The other images in the adequate-view group are assigned into the lumen-inspection group. Since the images in the fold-inspection group are positively correlated with ADR and APC, the time of the fold-inspection group elapsed during colonoscopy examination can be used as the main parameter for colonoscopy performance evaluation.

After all of the colonoscopy images are assigned, the elapsed time of the fold-inspection group, the lumen-inspection group, and/or the inadequate-view group may be obtained. The resulting elapsed time, the ratio of the resulting elapsed time over the total duration of the colonoscopy, and/or the ratio of the resulting elapsed time over the total duration of colonoscopy withdrawal may be used as the evaluation parameter(s).

The three-group classification method of the present technical solution is logically clear and capable of classifying all possible colonoscopy images split frame by frame from a colonoscopy video promptly and reliably.

In a preferred embodiment of the present disclosure, the step of (S22) includes a step of assigning the colonoscopy image into the fold-inspection group if the colonoscopy image meets one of the requirements of: (R1) colonic wall is shown, but in absence of haustrum or colonic lumen; (R2) colonic wall and haustrum are shown, but in absence of colonic lumen; and (R3) colonic wall, haustrum and colonic lumen are shown, the amount of the haustrum shown falls within a range of 1 to 5, and the colonic lumen falls outside of a central area of the colonoscopy image. Alternatively, if the image does not meet any of the requirements of (R1)-(R3), the colonoscopy image would be assigned into the lumen-inspection group.

The second classification criterion is defined for identification of the colonic wall, the haustrum, and/or the colonic lumen shown in the image. Specifically, if the image in the adequate-view group only shows the colonic wall, but in absence of the haustrum or the colonic lumen, the image would be assigned into the fold-inspection group. If the image in the adequate-view group shows the colonic wall and the haustrum, but in absence of the colonic lumen, the image would be assigned into the fold-inspection group. If the image in the adequate-view group shows the colonic wall, the colonic lumen, and 1-5 haustra, with the colonic lumen falling outside of the central area of the image, the image would be assigned into the fold-inspection group, as well. The rest of the images in the adequate-view group are assigned into the lumen-inspection group.

In the prior art, spiral colonoscopy requires the endoscope to be aimed at the colonic wall so as to allow inspection of the colonic mucosa. Consequently, common practice in the art has been to regard colonoscopy images showing the colonic lumen as invalid images with no statistical significance. However, regression analysis by the inventors revealed that even if the colonic lumen is shown in colonoscopy images meeting the requirement of (R3), those images can still be classified as valid images that positively correlate with ADR/APC, thus be assigned to the fold-inspection group. By assigning qualified lumen-showing colonoscopy images into the fold-inspection group, a more reasonable quality assessment approach is achieved. The method gives physicians more flexibility in performing colonoscopy and reduces undesired time spent on blindly adjusting the colonoscope.

In some embodiments, the second classification criterion includes a first classifier for determining the presence of haustrum in the image; for images in the adequate-view group not showing any haustrum, the first classifier would assign those images into the fold-inspection group. The rest of the images in the adequate-view group are further assigned according to a second classifier, in which whether the amount of haustrum shown is less than 3 would be determined. For images that show less than 3 haustra, a third classifier for determining the presence of colonic lumen in the image would further assign the images that are in absence of the colonic lumen into the fold-inspection group; for those showing less than 3 haustra and a colonic lumen, a fourth classifier for determining the position of the colonic lumen would assign the images having the colonic lumen falling outside of the central area of the image into the fold-inspection group, and assign the images having the colonic lumen locating inside of the central area of the image into the lumen-inspection group.

Alternatively, for images that show greater than or equal to 3 haustra, the third classifier would further assign the images that are in absence of the colonic lumen into the fold-inspection group; the fourth classifier would further assign the images that show the colonic lumen locating inside of the central area of the image into the lumen-inspection group; and a fifth classifier for determining whether the amount of the haustrum is no more than 5 would further classify the images showing the colonic lumen falling outside of the central area of the image. For those showing no more than 5 haustra, the images would be assigned into the fold-inspection group; conversely, the rest of images would be assigned into the lumen-inspection group. In one or more embodiments, the first classification criterion and/or the second classification criterion may be applied in a decision tree, in which the first to fifth classifiers are the decision nodes on the decision tree.

Furthermore, the central area of the colonoscopy image defined in the requirement of (R3) may be a circular area centered at the center of the colonoscopy image and having a radius of 0.1-0.5 fold of the radius of the colonoscopy image. In this technical solution, the central area of the colonoscopy image is a circular area that is centered at the center of the colonoscopy image and has a radius r. Preferably, the radius r of the central area is 0.1 to 0.5 fold of the radius R of the colonoscopy image, and is more preferably equal to 0.2 R. When the shape of the colonic lumen shown in the colonoscopy image is regular in general, e.g., substantially circular, the center of the regular shape is regarded the center of the colonic lumen. Alternatively, when the shape of the colonic lumen shown in the colonoscopy image is irregular, the center of the minimum bounding rectangle relative to the colonic lumen is regard the center of the colonic lumen. In cases where the center of the colonic lumen is inside of the central area of the colonoscopy image, the colonic lumen would be determined to locate inside of the central area of the colonoscopy image; conversely, in cases where the center of the colonic lumen is outside of the central area of the colonoscopy image, the colonic lumen would be determined to fall outside of the central area of the colonoscopy image.

In a preferred embodiment of the present disclosure, the step of (S21) includes a step of assigning the colonoscopy image into the inadequate-view group if the colonoscopy image meets one of the requirements of: (R4) a blurred area is shown and occupies more than half of a total area of the colonoscopy image; (R5) a reflection or a bubble is shown and occupies more than half of the total area of the colonoscopy image; (R6) fecal occlusion is shown and occupies more than half of the total area of the colonoscopy image; and (R7) wrinkled colonic wall is shown. Alternatively, if the colonoscopy image does not meet any of the requirements of (R4)-(R7), the colonoscopy image is assigned into the adequate-view group.

The elapsed time of the inadequate-view group corresponds to the duration of invalid inspection. Therefore, images that are mostly blurred, due to fast motion of the colonoscope, close proximity between the colonoscope and the colonic wall, water absorption or staining in the colonic track, and the like, would be assigned into the inadequate-view group. Images that are clear but mostly covered by reflection caused by foreign objects or occluded by bubble or feces would be assigned into the inadequate-view group. Further, images that are clear and not occluded but show wrinkled colonic wall would also be assigned into the inadequate-view group. Once the colonoscopy images meeting the aforementioned requirements are all assigned into the inadequate-view group, the rest would be assigned into the adequate-view group.

Furthermore, the evaluation method may further include a step of reassigning a colonoscopy image assigned to the inadequate-view group into the fold-inspection group if the colonoscopy image meets one of the requirements of: (R8) colonic wall is clearly shown, but in absence of haustrum or colonic lumen, and (R9) colonic wall and haustrum are clearly shown, but in absence of colonic lumen.

The inventors verified that although some images in the inadequate-view group had more than half of their total area being blurred, overexposed or occluded, the clear parts of the image may still show valid views of the colonic wall or haustrum. Therefore, the present technical solution may be further configured to reassign these images into the fold-inspection group, thereby measuring the elapsed time of valid images more accurately and allowing a more objective assessment of the physician's colonoscopy performance. In some embodiments, the reassignment step may be carried out after the first classification criterion is applied, or after the first and second classification criteria are both applied.

Furthermore, the evaluation method may further include a step of generating a marking for each of the assigned colonoscopy images; the marking is configured to identify the group to which the image is assigned. In addition to rating physicians' colonoscopy performance, the evaluation method may further be configured to display the generated marking on each colonoscopy image. The marked colonoscopy images are then used to update the colonoscopy video in real time, which allows the physician to be informed of the status of his/her operation during the colonoscopy examination, thereby guiding and improving the physician's colonoscopy operation.

The present disclosure also provides an artificial intelligent system for evaluating colonoscopy performance using the aforementioned evaluation methods. The system includes an input device configured to acquire a video during a colonoscopy examination; and a computing device in communication with the input device. The computing device includes a server having a processor and a memory coupled to the processor. The memory contains a computer program stored in. When the computer program is executed, the processor is controlled to perform the steps of:

(S1) splitting the video into a plurality of colonoscopy images;

(S2) assigning each of the colonoscopy images into a fold-inspection group or a non-fold-inspection group according to a first classification criterion and a second classification criterion, wherein the first classification criterion includes at least one of clarity, exposure, level of tissue wrinkling, and level of occlusion in each of the colonoscopy images; and the second classification criterion includes at least one of an amount of haustrum, an amount of colonic lumen, and a position of the colonic lumen in each of the colonoscopy images; and (S3) determining a performance rating of the colonoscopy examination according to an elapsed time of the fold-inspection group.

Specifically, the processor is configured to split the colonoscopy video acquired by the input device into a plurality of static colonoscopy images, each of which may correspond to one frame of the video. The processor is also configured to assign each of the images into either the fold-inspection group or a non-fold-inspection group according to the first classification criterion and the second classification criterion. The processor is further configured to determine the elapsed time of the fold-inspection group, by for example multiplying the amount of images in the fold-inspection group by the length of time per image, and to determine a performance rating of the colonoscopy examination recorded by the video according to the resulting elapsed time.

In classifying the colonoscopy images, the processor may be configured to assign, according to the first classification criterion, each of the colonoscopy images into an inadequate-view group or an adequate-view group and to assign, according to the second classification criterion, each image in the adequate-view group into the fold-inspection group or a lumen-inspection group.

The system may further include an output device in communication with the computing device and for displaying information associated with the colonoscopy performance, such as type of current view, the elapsed time or time ratio of the fold-inspection group and/or other groups, the elapsed time of the colonoscopy examination, therefore allowing the physician to be informed of the status of his/her operation and be guided throughout the colonoscopy procedure.

The present disclosure also provides a non-transitory computer-readable medium for evaluating colonoscopy performance using the aforementioned evaluation methods. The medium includes a computer program stored therein. When the computer program is executed, the device installing the non-transitory computer-readable medium is controlled to perform the evaluation methods described above.

Compared with the prior art, the invention provided in the present disclosure has the following advantages and beneficial effects:

1. The evaluation method provided in the present disclosure uses the elapsed time of the fold-inspection group as the evaluation parameter to establish a scientific and reliable standard for quality assessment of colonoscopy performance. The method is also an effective tool for guiding physicians to adjust his/her colonoscopy operation real-time so as to increase the time for collecting images qualified for the fold-inspection group, therefore improving the quality of the colonoscopy examination.

2. The method frees physicians from having to comply with conventional requirements associated with spiral colonoscopy, and encourage them to focus on acquiring more valid images within a shorter amount of examination time, which would help reduce discomfort of the examinee as well.

3. By assigning qualified lumen-showing colonoscopy images into the fold-inspection group, a more reasonable quality assessment approach is achieved. The method gives physicians more flexibility in performing colonoscopy and reduces undesired time spent on blindly adjusting the colonoscope.

4. By reassigning qualified images in the inadequate-view group into the fold-inspection group, the method can measure the elapsed time of valid images more accurately and allow a more objective assessment of the physician's colonoscopy performance.

5. By updating in real time the images acquired during colonoscopy examinations with proper markings showing the result of each image assignment, the method allows the physician to be informed of the status of his/her operation, thereby guiding and improving the physician's colonoscopy performance.

BRIEF DESCRIPTION OF THE DRAWINGS

The present invention will become more readily apparent to those ordinarily skilled in the art after reviewing the following detailed description and accompanying drawings, in which.

DETAILED DESCRIPTION OF THE PREFERRED EMBODIMENTS

The present invention will now be described more specifically with reference to the following embodiments. It is to be noted that the following descriptions of preferred embodiments of this invention are presented herein for purpose of illustration and description only. It is not intended to be exhaustive or to be limited to the precise form disclosed.

In the description of the present disclosure, it should be understood that terms for expressing direction such as front, rear, left, right, up, down, vertical, horizontal, high, low, inside, outside, etc. are used to explain the orientation or position with reference to the drawings, are intended merely to simplify the description of the present disclosure, rather than indicating or implying that the device or the element must be constructed or operated in such specific orientation or position, and therefore should not be construed as limiting the scope of the present disclosure.

Embodiment 1

Figure 1:
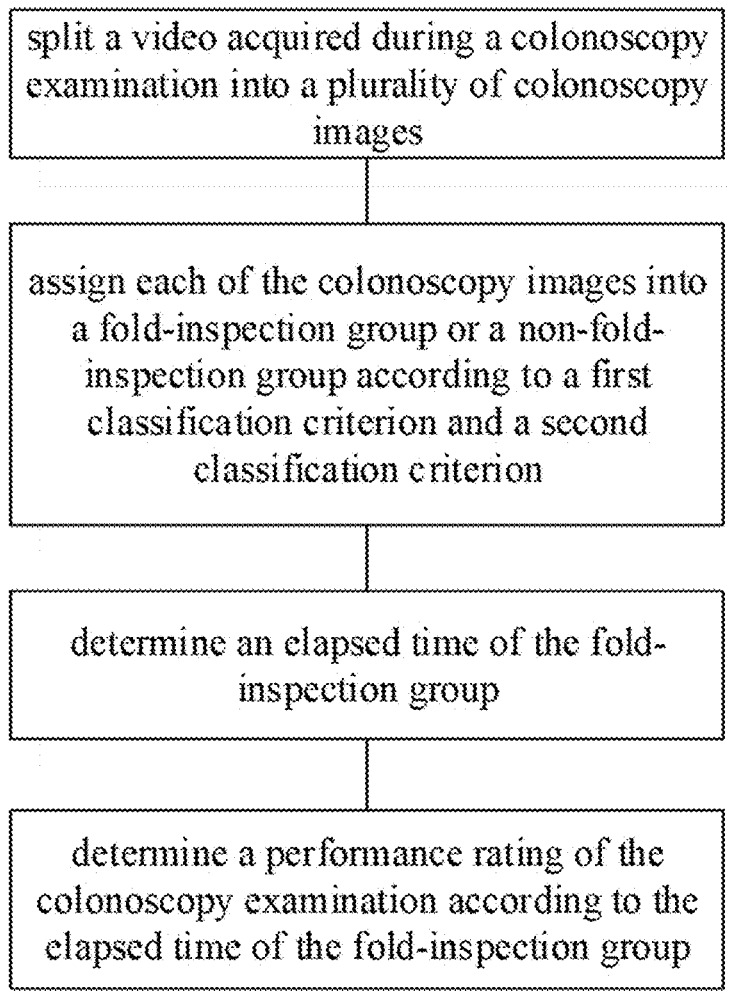
FIG. 1 is a flowchart of a method for evaluating colonoscopy performance according to one or more embodiments of the present disclosure.

As shown in FIG. 1, a method for evaluating colonoscopy performance according to an embodiment of the present disclosure includes the steps of:

(S1) splitting a video acquired during a colonoscopy examination into a plurality of colonoscopy images;

(S2) assigning each of the colonoscopy images into a fold-inspection group or a non-fold-inspection group according to a first classification criterion and a second classification criterion, wherein the first classification criterion includes at least one of clarity, exposure, level of tissue wrinkling, and level of occlusion in each of the colonoscopy images; and the second classification criterion includes at least one of an amount of haustrum, an amount of colonic lumen, and a position of the colonic lumen in each of the colonoscopy images; and (S3) determining a performance rating of the colonoscopy examination according to an elapsed time of the fold-inspection group.

In this embodiment, the video can be a real-time video and, after image classification, be added with markings in real time during the colonoscopy examination to instantly inform the physician of information such as the type of current view and the elapsed time of the fold-inspection group. In one or more embodiments, the video may also be a recorded video containing images of the entire colonoscopy examination. The video may be split frame by frame into a plurality of static colonoscopy images; given that the length of time per frame is known, the elapsed time of each assigned group may be obtained.

In some embodiments, the video may be acquired during the forward-viewing process or the withdrawal process.

In some embodiments, the video, in whole or in part, is split frame by frame into a plurality of static colonoscopy images, each of which is then assigned to a corresponding group to allow estimation of the elapsed time of different image types. In one or more embodiments, the video, in whole or in part, may be split at equal or predefined time intervals to obtain the colonoscopy images.

In this embodiment, the first classification criterion, which includes at least one of clarity, exposure, level of tissue wrinkling and level of occlusion in each of the colonoscopy images, is used to classify the colonoscopy images into either the adequate-view group or the inadequate-view group (a member of the non-fold-inspection group). The second classification criterion, which includes at least one of the amount of haustrum, the amount of colonic lumen, and the position of the colonic lumen in each of the colonoscopy images, is used to further classify the colonoscopy images in the adequate-view group into either the fold-inspection group or the lumen-inspection group (another member of the non-fold-inspection group). The amount of the colonic lumen refers to the amount of colonic lumen observable in the colonoscopy image, and is thus either 0 or 1; and the position of the colonic lumen is defined with respect to the central area of the colonoscopy image.

As the inventors verified, the images in the fold-inspection group are positively correlated with ADR and APC; the images in the lumen-inspection group have no statistically significant correlation with ADR or APC; and the images in the inadequate-view group are negatively correlated with ADR and APC. The correlation verification study is shown below in Embodiment 9.

In some embodiments, the first classification criterion and the second classification criterion can be used simultaneously or sequentially. For example, the second classification criterion may be used first to classify each colonoscopy image into either a preliminary fold-inspection group or a preliminary lumen-inspection group; the first classification criterion may then be used for classifying the images in the preliminary fold-inspection group into the fold-inspection group or the inadequate-view group, and for classifying the images in the preliminary lumen-inspection group into the lumen-inspection group or the inadequate-view group.

In some embodiments, in addition to the inadequate-view group and the lumen-inspection group, the non-fold-inspection group may further include subgroups derived from the inadequate-view group or the lumen-inspection group. For example, the inadequate-view group may be divided into a blurred image group, occluded image group, overexposed image group, and the like. Likewise, the lumen-inspection group may be divided according to the correlation of the images with ADR and APC.

In some embodiments, the step of assigning images into different group may be carried out by existing image recognition technology, such as wavelet moments or neural network based recognition algorithm. In one or more embodiments, a convolutional neural network (e.g., AlexNet) is trained to identify characteristics of colonoscopy images and classify the colonoscopy images accordingly. Specifically, pre-classified colonoscopy images are used as training datasets to train and validate the convolutional neural network, which is then used for image classification and/or assignment in the embodiments of the present disclosure.

Once the colonoscopy images are assigned into the respective groups, the elapsed time of the fold-inspection group may be determined to allow rating of the performance of the colonoscopy examination.

In one or more embodiments, the elapsed time of the fold-inspection group is used as the evaluation parameter. In one or more embodiments, the ratio of the elapsed time of the fold-inspection group over the total duration of the colonoscopy examination is used as the evaluation parameter.

In some embodiments, the elapsed time of both the fold-inspection group and the lumen-inspection group are obtained; and the elapsed time of the fold-inspection group is used as the main evaluation parameter, while the elapsed time of the lumen-inspection group is used as an auxiliary parameter. In one or more embodiments, the elapsed time of the inadequate-view group may also be counted to reflect the length of invalid inspection time of the colonoscopy examination, thereby evaluating the colonoscopy performance more comprehensively.

The evaluation method provided in this embodiment uses the elapsed time of the fold-inspection group as the evaluation parameter to establish a scientific and reliable standard for quality assessment of colonoscopy performance. The method also presents an effective tool for guiding physicians to adjust his/her colonoscopy operation so as to increase the time for collecting images qualified for the fold-inspection group, therefore improving the quality of the colonoscopy examination.

Embodiment 2

In addition to the features of Embodiment 1, this embodiment applies the first classification criterion prior to applying the second classification criterion.

In this embodiment, the image assignment step (S2) includes: (S21) assigning each of the colonoscopy images into an inadequate-view group or an adequate-view group according to the first classification criterion; and (S22) assigning each image in the adequate-view group into the fold-inspection group or a lumen-inspection group according to the second classification criterion. The rating step (S3) includes: determining the performance rating of the colonoscopy examination according to an elapsed time of at least one of the fold-inspection group, the lumen-inspection group, and the inadequate-view group.

The three-group classification method provided herein is logically clear and capable of classifying all possible colonoscopy images split frame by frame from a colonoscopy video promptly and reliably.

After all the colonoscopy images are assigned, the elapsed time of the fold-inspection group, the lumen-inspection group, and/or the inadequate-view group may be obtained. The resulting elapsed time or the ratio of the elapsed time over the total duration of the colonoscopy examination may be used as the parameter for performance evaluation.

Figure 2:
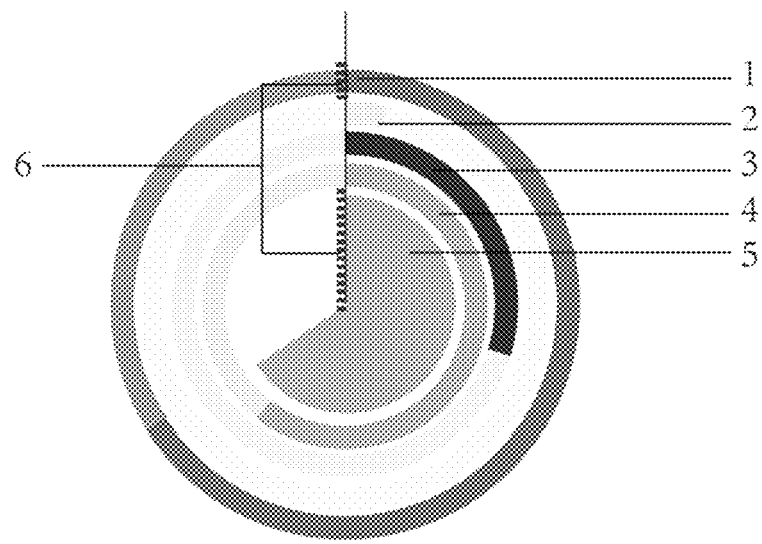
FIG. 2 is a circular chart exemplifying a timer for indicating the elapsed time of each group according to one or more embodiments of the present disclosure.

In one or more embodiments, as shown in FIG. 2, the method may further include a step of displaying the elapsed time of the colonoscopy examination and the elapsed time and/or time ratio of one or more of the groups. For example, a circular chart may be used to display, instantly or retrospectively, the elapsed time of the fold-inspection group, the lumen-inspection group, and the inadequate-view group, as well as the elapsed time of colonoscope withdrawal; a reference marking indicating the minimum time required for the fold-inspection group may also be displayed to facilitate understanding of the performance goal. In FIG. 2, reference numeral 1 denotes an exemplary progress bar showing the elapsed time for colonoscope withdrawal, reference numeral 2 denotes an exemplary progress bar showing the elapsed time of the lumen-inspection group, reference numeral 3 denotes an exemplary progress bar showing the elapsed time of the inadequate-view group, reference numeral 4 denotes an exemplary progress bar showing the elapsed time of the fold-inspection group, reference numeral 5 denotes an exemplary progress bar showing the elapsed number of frames of the fold-inspection group, and the reference numeral 6 denotes exemplary standard lines that may be adjusted respectively according to the total time required for colonoscope withdrawal and the total number of frames required for the fold-inspection group.

Figure 3:
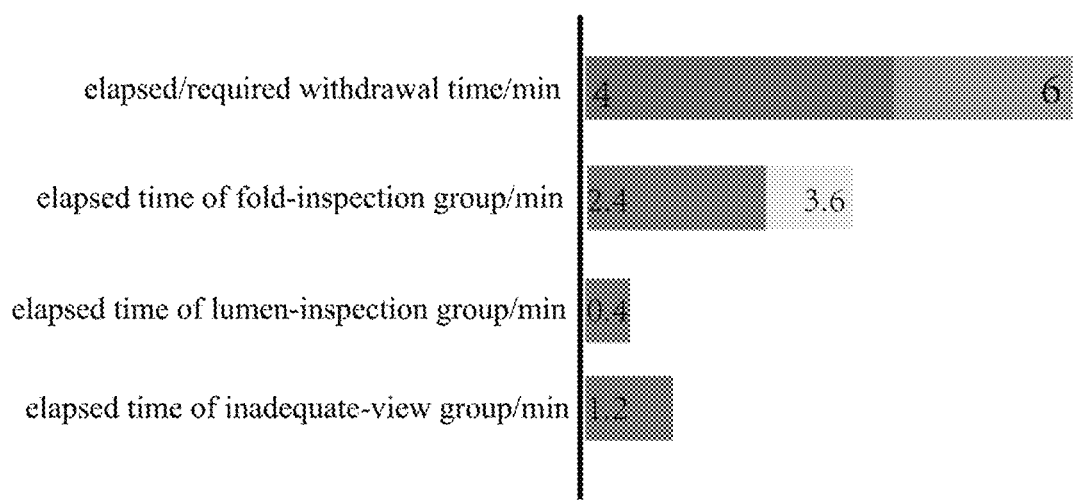
FIG. 3 is a bar chart exemplifying another timer for indicating the elapsed time of each group according to one or more embodiments of the present disclosure.

In one embodiment, as shown in FIG. 3, a bar chart may also be used to display, instantly or retrospectively, for example, the elapsed time of colonoscope withdrawal, the required time for colonoscope withdrawal, the minimum required time for the fold-inspection group, the elapsed time of the fold-inspection group, the elapsed time of the lumen-inspection group, and the elapsed time of the inadequate-view group. In one embodiment, the total duration of the colonoscopy examination including the forward-viewing process and the withdrawal process may also be displayed.

Embodiment 3

In addition to the features of the aforementioned embodiments, the image assignment step (S22) may include: assigning the colonoscopy image in the adequate-view group into the fold-inspection group if the image meets one of the requirements of: (R1) colonic wall is shown, but in absence of haustrum or colonic lumen; (R2) colonic wall and haustrum are shown, but in absence of colonic lumen; and (R3) colonic wall, haustrum and colonic lumen are shown, the amount of the haustrum shown falls within a range of 1 to 5, and the colonic lumen falls outside of a central area of the image. Alternatively, if the colonoscopy image does not meet any of the requirements of (R1)-(R3), the image is assigned into the lumen-inspection group.

Figure 4:
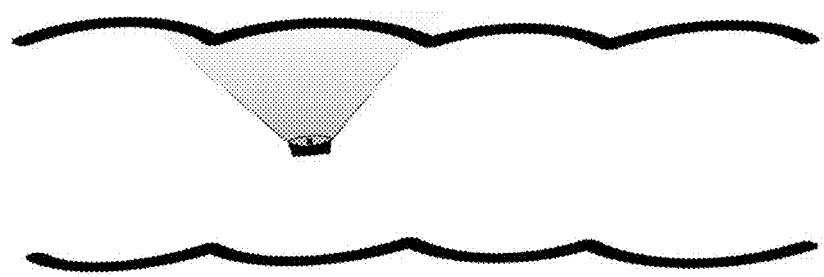
FIG. 4 depicts a cross-sectional view of a colonic segment with a colonoscope aiming at the colonic wall.
Figure 5:
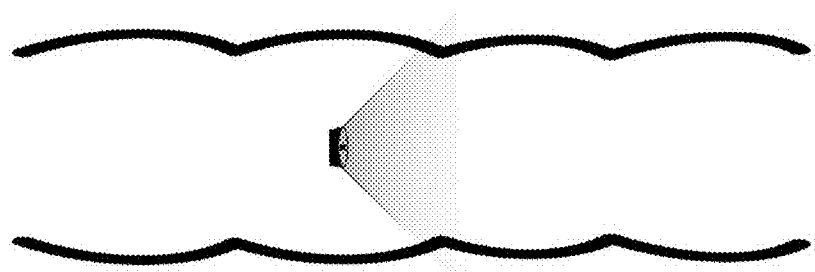
FIG. 5 depicts is a cross-sectional view of a colonic segment with the colonoscope aiming at the colonic lumen.
Figure 6:
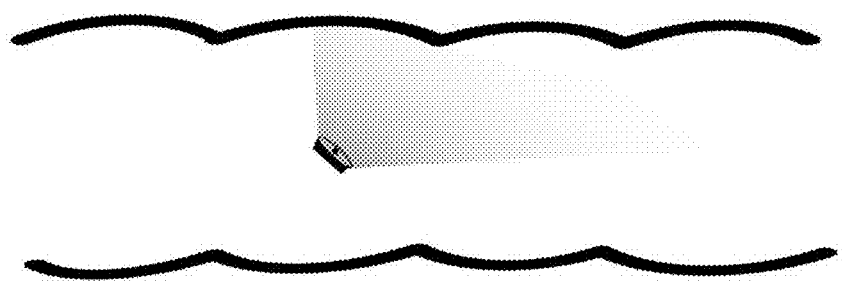
FIG. 6 depicts is a cross-sectional view of a colonic segment with the colonoscope aiming toward the colonic wall, the image captured by which would show the colonic lumen locating outside of the central area of the image.

In conventional spiral colonoscopy, physicians are required to inspect the colonic mucosa by aiming the colonoscope straight at the colonic wall, as illustrated in FIG. 4. Therefore, common practice in the art has been to regard colonoscopy images taken by aiming the colonoscope toward the colonic lumen or the colonic wall (as shown in FIGS. 5 and 6), thus showing the colonic lumen, as invalid images with no statistical significance. However, regression analysis by the inventors revealed that for colonoscopy images meeting the requirement of (R3), even if the colonic lumen is shown, as long as the colonic lumen does not fall inside of the central area of the image, those images can still be classified as valid images that positively correlate with ADR/APC, thus be assigned to the fold-inspection group; only in cases where the colonic lumen falls inside of the central area of the image, those images would have no statistically significant correlation with ADR or APC, thus be assigned to the lumen-inspection group. By assigning qualified lumen-showing colonoscopy images into the fold-inspection group, a more reasonable quality assessment approach is achieved. The method gives physicians more flexibility in performing colonoscopy and reduces undesired time spent on blindly adjusting the colonoscope.

Figure 7:
FIG. 7 shows a colonoscopy image assigned into the fold-inspection group according to one or more embodiments of the present disclosure.
Figure 8:
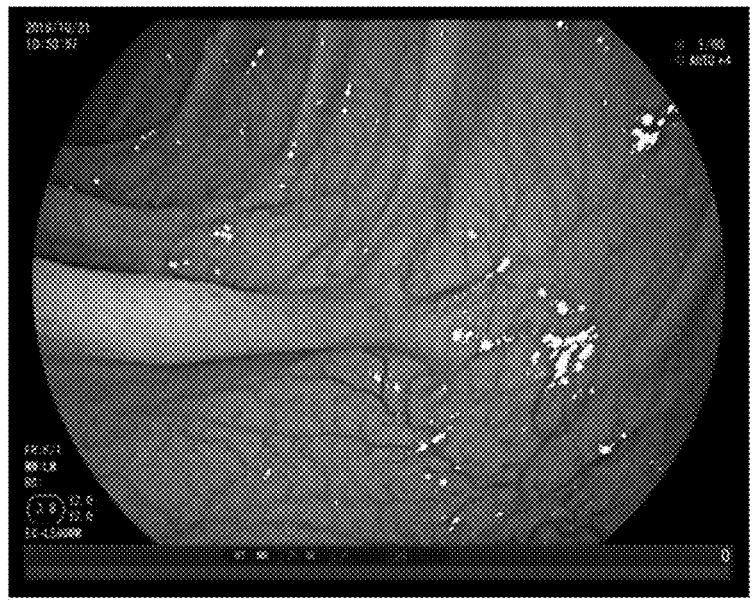
FIG. 8 shows another colonoscopy image assigned into the fold-inspection group according to one or more embodiments of the present disclosure.
Figure 9:
FIG. 9 shows still another colonoscopy image assigned into the fold-inspection group according to one or more embodiments of the present disclosure.

FIG. 7 to FIG. 9 shows three representative images of the fold-inspection group. Specifically, the image in FIG. 7 only shows the colonic wall, but in absence of the haustrum or the colonic lumen; the image in FIG. 8 shows the colonic wall and the haustra, but in absence of the colonic lumen; and the image in FIG. 9 shows the colonic wall, less than 5 haustra, and the colonic lumen falling outside of the central area of the image. By applying the second classification criterion, images in the adequate-view group that meet the requirements (R1)-(R3), as exemplified in FIGS. 7-9, would be assigned into the fold-inspection group; the remaining images in the adequate-view group would be assigned into the lumen-inspection group.

Figure 10:
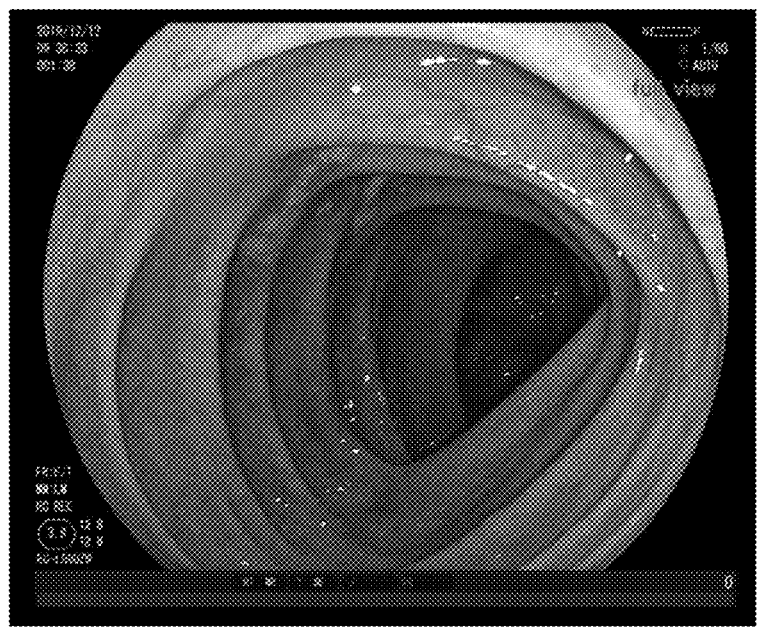
FIG. 10 shows a colonoscopy image assigned into the lumen-inspection group according to one or more embodiments of the present disclosure.

FIG. 10 shows a representative image of the lumen-inspection group. Images assigned into the lumen-inspection group would show the colonic wall, the haustrum, and the colonic lumen locating inside of the central area of the image.

Figure 11:
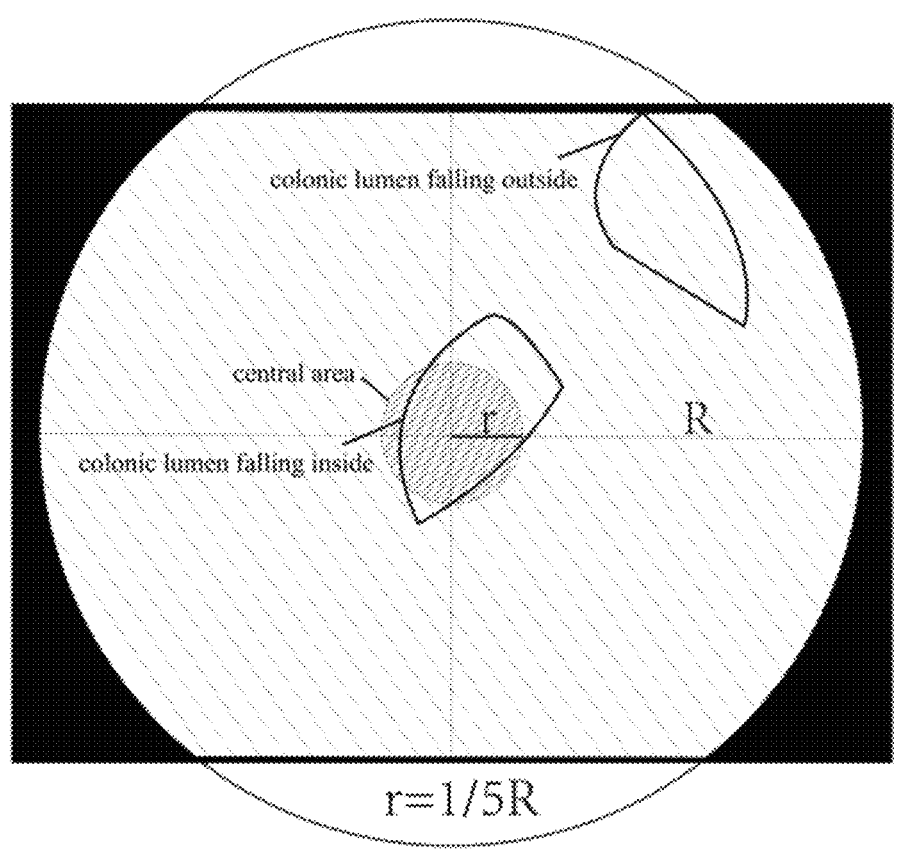
FIG. 11 is a schematic illustration of a colonoscopy image with the colonic lumen locating inside or outside of the central area of the colonoscopy image according to one or more embodiments of the present disclosure.

In some embodiments, as exemplified in FIG. 11, the central area of the image defined in the requirement of (R3) may be a circular area centered at a center of the image and having a radius r of 0.1-0.5 fold, preferably 0.2 fold, of the radius R of the image. As illustrated, the colonoscopy image typically does not display the complete circular lens view; therefore, the radius of the colonoscopy image may refer to the radius of the complete circle of the lens view. If the shape of the colonic lumen shown in the colonoscopy image is regular in general, e.g., substantially circular, the center of the regular shape may be regarded as the center of the colonic lumen. Alternatively, if the shape of the colonic lumen shown in the colonoscopy image is irregular, the center of the minimum bounding rectangle relative to the colonic lumen may be regarded as the center of the colonic lumen. In cases where the center of the colonic lumen is inside of the central area of the colonoscopy image, the colonic lumen would be determined to locate inside of the central area of the colonoscopy image; conversely, in cases where the center of the colonic lumen is outside of the central area of the colonoscopy image, the colonic lumen would be determined to fall outside of the central area of the colonoscopy image.

Embodiment 4

In addition to the features of Embodiment 3, the image assignment step (S21) may include: assigning the image into the inadequate-view group if the image meets one of the requirements of: (R4) a blurred area is shown and occupies more than half of a total area of the image; (R5) a reflection or a bubble is shown and occupies more than half of the total area of the image; (R6) fecal occlusion is shown and occupies more than half of the total area of the image; and (R7) wrinkled colonic wall is shown. Alternatively, if the image does not meet any of the requirements of (R4)-(R7), the image is assigned into the adequate-view group.

Figure 12:
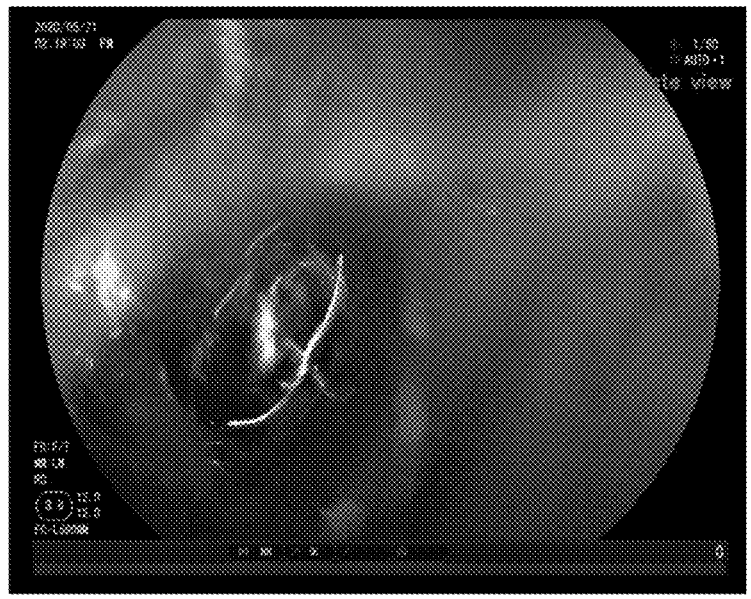
FIG. 12 shows a colonoscopy image assigned into the inadequate-view group according to one or more embodiments of the present disclosure.
Figure 13:
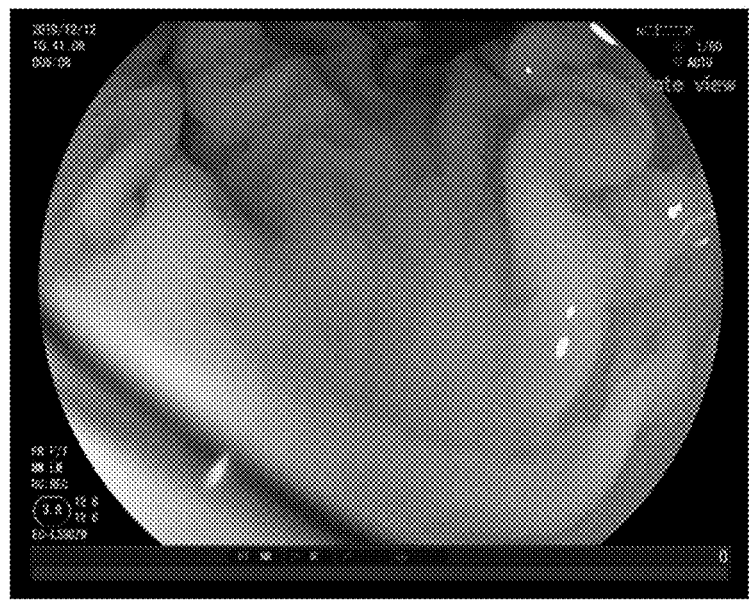
FIG. 13 shows another colonoscopy image assigned into the inadequate-view group according to one or more embodiments of the present disclosure.

FIG. 12 and FIG. 13 are two representative images of the inadequate-view group. As exemplified in FIG. 12, more than half of the total area of the image is blurred due to water ingestion, making it impossible to properly inspect the colonic mucosa. As exemplified in FIG. 13, the colonic wall shown in the image is wrinkled and does not properly expose the colonic mucosa for inspection.

Embodiment 5

Figure 14:
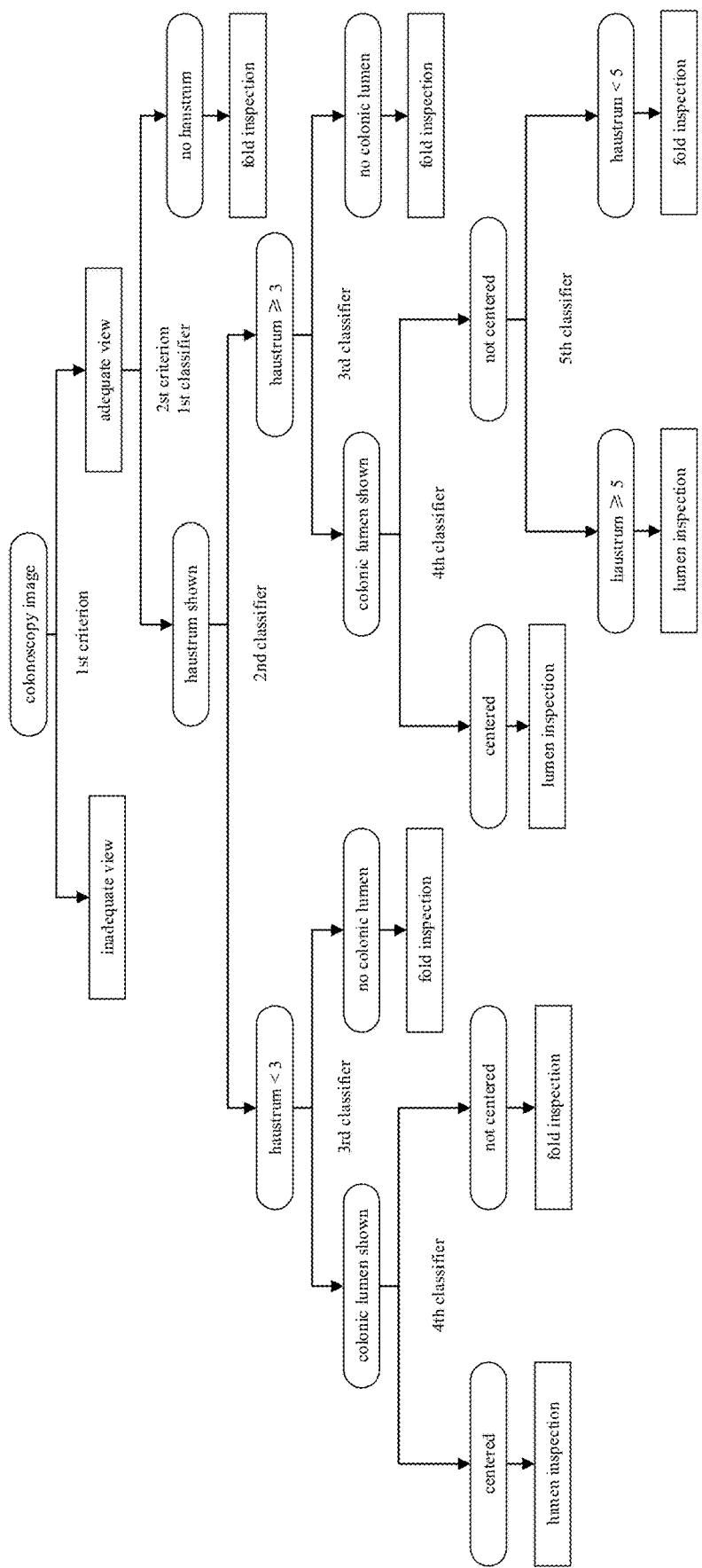
FIG. 14 depicts a decision tree for classifying colonoscopy images according to one or more embodiments of the present disclosure.

In addition to the features of Embodiments 3 and 4, the first classification criterion and the second classification criterion may be applied to a decision tree structure, as shown in FIG. 14, for classifying the colonoscopy images.

Specifically, the first classification criterion may be used as the first decision node of the decision tree to classify the colonoscopy images into either the inadequate-view group or the adequate-view group.

Next, in applying the second classification criterion, the first classifier may be adopted for determining the presence of haustrum in the image. For images in the adequate-view group not showing any haustrum, the first classifier would assign those images into the fold-inspection group. The rest of the images in the adequate-view group are further assigned according to the second classifier, in which whether the amount of haustrum shown is less than 3 would be determined. For images that show less than 3 haustra, the third classifier for determining the presence of colonic lumen in the image would further assign the images that are in absence of the colonic lumen into the fold-inspection group; for those showing less than 3 haustra and a colonic lumen, a fourth classifier for determining the position of the colonic lumen would assign the images having the colonic lumen falling outside of the central area of the image into the fold-inspection group, and assign the images having the colonic lumen locating inside of the central area of the image into the lumen-inspection group.

Alternatively, for images that show greater than or equal to 3 haustra, the third classifier would further assign the images that are in absence of the colonic lumen into the fold-inspection group; the fourth classifier would further assign the images that show the colonic lumen locating inside of the central area of the image into the lumen-inspection group; and a fifth classifier for determining whether the amount of the haustrum is no more than 5 would further classify the images showing the colonic lumen falling outside of the central area of the image. For those showing no more than 5 haustra, the images would be assigned into the fold-inspection group; conversely, the rest of images would be assigned into the lumen-inspection group.

In some embodiments, after the colonoscopy images are assigned through the first classification criterion or both the first and second classification criteria, some of those regarded as containing invalid views may be reconsidered and reclassified as to contain valid views. Specifically, the images in the inadequate-view group may be reassigned into the fold-inspection group if the images meet one of the requirements of: (R8) colonic wall is clearly shown, but in absence of haustrum or colonic lumen, and (R9) colonic wall and haustrum are clearly shown, but in absence of colonic lumen.

Embodiment 6

In addition to the features of the aforementioned embodiments, the evaluation method may further include a step of generating a marking for each of the assigned colonoscopy images. The marking may be configured to allow identification of the group to which the image is assigned, and be used to update, instantly or retrospectively, the video acquired during colonoscopy examination.

In this embodiment, the evaluation method may further include generating the marking for each colonoscopy image and display the marking on each colonoscopy image to identify the group to which the image is assigned. As shown in FIGS. 10, 12 and 13, a status label (as highlighted by white solid line) may be added to the upper right corner of the colonoscopy image to indicate the group to which the image is assigned. For example, the colonoscopy image shown in FIG. 10 is assigned into the lumen-inspection group and may be labeled as having a "full view" whereas the colonoscopy image shown in FIG. 12 or FIG. 13 is assigned into the inadequate-view group and may be labeled as having an "inadequate view."

The marked colonoscopy images may be used to update the colonoscopy video in real time, which allows the physician to be informed of the status of his/her operation during the colonoscopy examination, thereby guiding and improving the physician's colonoscopy operation.

In some embodiments, assignment of the colonoscopy images may be accomplished by the neural network trained for colonoscopy image classification. Upon completion of image assignment, the images may be marked to indicate the group to which the image is assigned, and be written back into the same frame of the colonoscopy video. In one or more embodiments, the images may further be marked to indicate the elapsed time of colonoscope withdrawal, the total duration of the colonoscopy, the elapsed time of the fold-inspection group, the lumen-inspection group and the inadequate-view group, and/or the ratio of each elapsed time over the total duration of the colonoscopy or colonoscope withdrawal.

Embodiment 7

An artificial intelligent system for evaluating colonoscopy performance based on the aforementioned embodiments may include an input device and a computing device. The input device is configured to acquire a video during a colonoscopy examination. The computing device is in communication with the input device, and includes a server having a processor and a memory coupled to the processor. The memory contains a computer program stored therein. When the computer program is executed, the processor is controlled to perform the steps of:

(S1) splitting the video into a plurality of colonoscopy images;

(S2) assigning each of the colonoscopy images into a fold-inspection group or a non-fold-inspection group according to a first classification criterion and a second classification criterion, wherein the first classification criterion includes at least one of clarity, exposure, level of tissue wrinkling, and level of occlusion in each of the colonoscopy images; and the second classification criterion includes at least one of an amount of haustrum, an amount of colonic lumen, and a position of the colonic lumen in each of the colonoscopy images; and (S3) determining a performance rating of the colonoscopy examination according to an elapsed time of the fold-inspection group.

Specifically, the processor is configured to split the colonoscopy video acquired by the input device into a plurality of static colonoscopy images, each of which may correspond to one frame of the video. The processor is also configured to assign each of the colonoscopy images into either the fold-inspection group or a non-fold-inspection group according to the first classification criterion and the second classification criterion. The processor is further configured to determine the elapsed time of the fold-inspection group, by for example multiplying the amount of images in the fold-inspection group by the length of time per image, and to determine a performance rating of the colonoscopy examination recorded by the video according to the resulting elapsed time.

In some embodiments, the processor may include a convolutional neural network trained for colonoscopy image recognition. The convolutional neural network may be trained and validated by using pre-classified colonoscopy images as the training datasets and used for image classification and/or assignment in the embodiments of the present disclosure.

In one or more embodiments, the processor may also be configured to assign, according to the first classification criterion, each of the colonoscopy images into the inadequate-view group or the adequate-view group and to assign, according to the second classification criterion, each image in the adequate-view group into the fold-inspection group or a lumen-inspection group.

The system may further include an output device in communication with the computing device and for displaying information associated with the colonoscopy performance, such as type of current view, the elapsed time or time ratio of the fold-inspection group and/or other groups, and the elapsed time of the colonoscopy examination, therefore allowing the physician to be informed of the status of his/her operation and be guided throughout the colonoscopy procedure.

Embodiment 8

A non-transitory computer-readable medium for evaluating colonoscopy performance using the aforementioned embodiments may include a computer program stored therein; when the computer program is executed, the device installing the non-transitory computer-readable medium is controlled to perform the aforementioned evaluation methods.

In this embodiment, the computer program is configured to control the device to perform all or part of the evaluation method. The computer program includes computer program codes, which may be source codes, object codes, executable files or other intermediate forms. The non-transitory computer-readable medium may include any entity or device, recording medium, USB flash drive, mobile hard disk, magnetic disk, optical disk, computer memory, read-only memory (ROM), random access memory (RAM), electrical carrier signal, telecommunication signal and software distribution medium.

Embodiment 9

The experiment described below was conducted to verify the correlation between the fold-inspection group, the lumen-inspection group, and the inadequate-view group with ADR and APC.

Verification

A total of 1225 patients between the age of 18-75 who were referred to one of four endoscopy centers in China between Sep. 2, 2019 and May 29, 2020 for colonoscopic diagnosis, screening, and monitoring were included in the study. Patients with history of inflammatory bowel disease (IBD), colorectal cancer (CRC), colorectal surgery, or contraindication for biopsy were excluded. Patients having highly suspicious polyposis syndrome, IBD or CRC tumor, but with unaffected cecum, were also excluded. Patients associated with unsuccessful pathology tests due to insufficient tissues extracted by cold forceps biopsy were excluded, as well. Written informed consents were obtained from all participants before the colonoscopy procedure.

All polyps were biopsied or removed by cold forceps biopsy once verified by the operating physician. All biopsies were sent for pathology examination. In a typical workflow of the majority of endoscopy centers in China, large polyps would be biopsied prior to complete resection. Diminutive (≤2 mm) rectal polyps detected under blue laser imaging (BLI) or Fuji intelligent chromoendoscopy (FICE) according to type 1 of NBI International Colorectal Endoscopic (NICE) Classification, were regarded as hyperplastic in nature and not biopsied. The location, size and morphological features of each detected polyp were recorded according to the Paris Classification.

Colonoscopy examinations were performed by using LASEREO and VP4450HD (Fujifilm, Tokyo, Japan), high definition colonoscopes (EC-L590, EC-580, EC-590) and high-definition monitors.

Bowel cleanliness was measured by Boston Bowel Preparation Scale (BBPS) during colonoscopy. The time for cecal insertion, colonoscope entry, colonoscope withdrawal, and biopsy of each lesion were recorded by a stopwatch during each colonoscopy procedure. Polyp size was estimated by open biopsy forceps. Biopsied polys were sent to a pathology diagnostic center for pathology diagnosis and subsequent statistical analysis.

Results

The artificial intelligent system according to the embodiments described above was used to analyze the videos acquired during the colonoscopy examinations and measure the elapsed time of the images qualifying the fold-inspection group, the lumen-inspection group, or the inadequate-view group. The elapsed time of the fold-inspection group corresponds to the duration of valid views of the colonic mucosa; the elapsed time of the lumen-inspection group corresponds to the duration of views of the colonic lumen; and the elapsed time of the inadequate-view group corresponds to the duration of invalid views of the colonic mucosa.

In this retrospective study, a total of 1225 patients were included. In order to ensure consistency among physicians' operations, 8 experienced physicians were invited to participate in the study. The average withdrawal time among the physicians was 6.06-7.85 min, meeting the time requirement of the international standard for colonoscope withdrawal (>6 min). The ADR, APC and polyp detection rate (PDR) of the participated physicians are shown in Table 1.

TABLE 1

| Physician | 1 | 2 | 3 | 4 | 5 | 6 | 7 | 8 |
| --- | --- | --- | --- | --- | --- | --- | --- | --- |
| PDR | 0.305 | 0.306 | 0.422 | 0.43 | 0.549 | 0.462 | 0.472 | 0.597 |
| ADR | 0.133 | 0.14 | 0.249 | 0.281 | 0.291 | 0.301 | 0.331 | 0.418 |
| APC | 0.19 | 0.202 | 0.439 | 0.456 | 0.408 | 0.442 | 0.409 | 0.955 |
| average withdrawal time (sec) | 431.381 | 470.884 | 455.104 | 399.188 | 366.966 | 363.994 | 424.228 | 410 |
| inadequate view time/ total colonoscopy time, % | | 57.31 | | | | 52.29 | | |
| lumen inspection time/ total colonoscopy time, % | | 22.1 | | | | 18.92 | | |
| fold inspection time/ total colonoscopy time, % | | 20.59 | | | | 28.78 | | |

According to the international standard, the average adenoma detection rate (ADR) of a qualified physician is required to be higher than 0.25. Therefore, the physicians were divided into a qualifying group and a non-qualifying group. According to the results shown in Table 1, physicians 1 to 3 were assigned to the non-qualifying group, and the other five physicians complying the international standard were assigned to the qualifying group. Statistical analysis revealed that for the colonoscopy images acquired by the three physicians in the non-qualifying group, the ratio of the elapsed time of the fold-inspection group over the total duration of the colonoscopy ranged from 18.08% to 25.53%, with the average time ratio being 20.59%, the average ADR being 0.174, and the average APC being 0.277. Further, the average ratio of the elapsed time of the lumen-inspection group over the total duration of the colonoscopy was 22.10%, and the average ratio of the elapsed time of the inadequate-view group over the total duration of the colonoscopy was 57.31%. For the five physicians in the qualifying group, the ratio of the elapsed time of the fold-inspection group over the total duration of the colonoscopy ranged from 25.73% to 30.84%, with the average time ratio being 28.78%, the average ADR being 0.325, and the average APC being 0.534. Further, the average ratio of the elapsed time of the lumen-inspection group over the total duration of the colonoscopy was 18.92%, and the average ratio of the elapsed time of the inadequate-view group over the total duration of the colonoscopy was 52.29%.

Assuming no statistical difference between the baselines, as compared with the non-qualifying group, the ADR of the qualifying group was about 1.87 folds higher, the APC was about 1.93 folds higher, the average time ratio of the fold-inspection group was about 1.4 folds higher, and the average time ratio of the inadequate-view group was about 0.91 fold. The results showed statistical differences between the performance of the two groups, suggesting that increased collection time for images qualified for the fold-inspection group can improve the ADR and APC of the physicians. Meanwhile, Table 1 also shows that the average withdrawal time of the physicians in the qualifying group was less than that of the physicians in the non-qualifying group, demonstrating that using colonoscope withdrawal time as the main parameter for performance evaluation is inaccurate and unreliable.

Further, Spearman rank correlation coefficient was used to measure in triplicate the correlation of elapsed time of the fold-inspection group, lumen-inspection group, and inadequate-view groups with ADR and APC of the physicians. As shown in Table 2, the results revealed that the elapsed time of the lumen-inspection group had no statistically significant correlation with ADR or APC (P>0.05), whereas the elapsed time for both the inadequate-view and fold-inspection groups showed statistically significant differences in correlation with ADR and APC (P<0.01). Assuming no statistical difference in withdrawal time, the elapsed time of the fold-inspection group was positively correlated with ADR, whereas the elapsed time of the inadequate-view group was negatively correlated with ADR. The results are yet another piece of evidence that shows the increase in elapsed time of the fold-inspection group can effectively increase exposure of the colonic mucosa to the physicians, thereby significantly improving the physicians' ADR and APC.

TABLE 2

| inadequate view time/total colonoscopy time | <0.526116 (N = 612) | >=0.526116 (N = 613) | P value |
|---|---|---|---|
| PDR | 0.521 | 0.341 | 0.001 |
| ADR | 0.319 | 0.188 | 0.001 |
| PPC (polyp per colonoscopy) | 1.273 | 0.706 | 0.001 |
| APC | 0.533 | 0.254 | 0.001 |
| lumen inspection time/total colonoscopy time | <0.207552 (N = 612) | >=0.207552 (N = 613) | P value |
| PDR | 0.448 | 0.414 | 0.239 |
| ADR | 0.266 | 0.24 | 0.286 |
| PPC | 1.033 | 0.946 | 0.128 |
| APC | 0.42 | 0.367 | 0.14 |
| fold inspection time/total colonoscopy time | <0.249325 | >=0.249325 | |

TABLE 2-continued

| colonoscopy time | (N = 612) | (N = 613) | P value |
|---|---|---|---|
| PDR | 0.322 | 0.54 | 0.001 |
| ADR | 0.16 | 0.346 | 0.001 |
| PPC | 0.703 | 1.276 | 0.001 |
| APC | 0.232 | 0.555 | 0.001 |
| withdrawal time | 415.724(90.448) | 418.863(118.809) | 0.603 |

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A computer-implemented method for evaluating colonoscopy performance, comprising steps of:
(S1) splitting a video acquired during a colonoscopy examination into a plurality of colonoscopy images;
(S2) assigning each of the colonoscopy images into an inadequate-view group or an adequate-view group according to a first classification criterion, and assigning each colonoscopy image in the adequate-view group into a fold-inspection group or a lumen-inspection group according to a second classification criterion,
wherein the first classification criterion comprises at least one of clarity, exposure, level of tissue wrinkling, and level of occlusion in each of the colonoscopy images; the second classification criterion comprises at least one of an amount of haustrum, an amount of colonic lumen, and a position of the colonic lumen in each of the colonoscopy images and
wherein the colonoscopy image in the adequate-view group is assigned into the fold-inspection group if the colonoscopy image meets one of the requirements of:
(R1) colonic wall is shown, but in absence of haustrum or colonic lumen;
(R2) colonic wall and haustrum are shown, but in absence of colonic lumen; and
(R3) colonic wall, haustrum and colonic lumen are shown, the amount of the haustrum shown falls within a range of 1 to 5, and the colonic lumen falls outside of a central area of the colonoscopy image; or
the colonoscopy image in the adequate-view group is assigned into the lumen-inspection group if the colonoscopy image does not meet any of the requirements of (R1)-(R3); and
(S3) determining a performance rating of the colonoscopy examination according to an elapsed time of at least one of the fold-inspection group, the lumen-inspection group, and the inadequate-view group.

2. The method of claim 1, wherein the requirement of (R3) is defined as a center of the colonic lumen falling outside of the central area of the colonoscopy image, and the central area of the colonoscopy image is defined as a circular area centered at a center of the colonoscopy image and having a radius of 0.1-0.5 fold of a radius of the colonoscopy image.

3. The method of claim 1, wherein the colonoscopy image is assigned into the inadequate-view group if the colonoscopy image meets one of the requirements of:

(R4) a blurred area is shown and occupies more than half of a total area of the colonoscopy image;
(R5) a reflection or a bubble is shown and occupies more than half of the total area of the colonoscopy image;
(R6) fecal occlusion is shown and occupies more than half of the total area of the colonoscopy image; and
(R7) wrinkled colonic wall is shown; or
the colonoscopy image is assigned into the adequate-view group if the colonoscopy image does not meet any of the requirements of (R4)-(R7).

4. The method of claim 3, further comprising:
reassigning a colonoscopy image assigned to the inadequate-view group into the fold-inspection group if the colonoscopy image meets one of the requirements of:
(R8) colonic wall is clearly shown, but in absence of haustrum or colonic lumen, and
(R9) colonic wall and haustrum are clearly shown, but in absence of colonic lumen.

5. The method of claim 1, further comprising:
generating a marking for each of the assigned colonoscopy images, wherein the marking identifies the group to which the colonoscopy image is assigned.

6. An artificial intelligent system for evaluating colonoscopy performance, comprising:
an input device configured to acquire a video during a colonoscopy examination; and
a computing device in communication with the input device, the computing device comprising a server having a processor and a memory coupled to the processor, the memory having a computer program stored therein, wherein when the computer program is executed, the processor is controlled to perform steps of:
(S1) splitting the video acquired by the input device into a plurality of colonoscopy images;
(S2) assigning each of the colonoscopy images into an inadequate-view group or an adequate-view group according to a first classification criterion, and assigning each colonoscopy image in the adequate-view group into a fold-inspection group or a lumen-inspection group according to a second classification criterion,
wherein the first classification criterion comprises at least one of clarity, exposure, level of tissue wrinkling, and level of occlusion in each of the colonoscopy images; the second classification criterion comprises at least one of an amount of haustrum, an amount of colonic lumen, and a position of the colonic lumen in each of the colonoscopy images and
wherein the colonoscopy image in the adequate-view group is assigned into the fold-inspection group if the colonoscopy image meets one of the requirements of:
(R1) colonic wall is shown, but in absence of haustrum or colonic lumen;
(R2) colonic wall and haustrum are shown, but in absence of colonic lumen; and
(R3) colonic wall, haustrum and colonic lumen are shown, the amount of the haustrum shown falls within a range of 1 to 5, and the colonic lumen falls outside of a central area of the colonoscopy image; or
the colonoscopy image in the adequate-view group is assigned into the lumen-inspection group if the colonoscopy image does not meet any of the requirements of (R1)-(R3); and
(S3) determining a performance rating of the colonoscopy examination according to an elapsed time of at least one of the fold-inspection group, the lumen-inspection group, and the inadequate-view group.

7. The system of claim 6, wherein the requirement of (R3) is defined as a center of the colonic lumen falling outside of the central area of the colonoscopy image, and the central area of the colonoscopy image is defined as a circular area centered at a center of the colonoscopy image and having a radius of 0.1-0.5 of a radius of the colonoscopy image.

8. The system of claim 6, wherein the colonoscopy image is assigned into the inadequate-view group if the colonoscopy image meets one of the requirements of:
(R4) a blurred area is shown and occupies more than half of a total area of the colonoscopy image;
(R5) a reflection or a bubble is shown and occupies more than half of the total area of the colonoscopy image;
(R6) fecal occlusion is shown and occupies more than half of the total area of the colonoscopy image; and
(R7) wrinkled colonic wall is shown; or
the colonoscopy image is assigned into the adequate-view group if the colonoscopy image does not meet any of the requirements of (R4)-(R7).

9. The system of claim 8, wherein when the computer program is executed, the processor is controlled to further perform steps of:
reassigning a colonoscopy image assigned to the inadequate-view group into the fold-inspection group if the colonoscopy image meets one of the requirements of:
(R8) colonic wall is clearly shown, but in absence of haustrum or colonic lumen, and
(R9) colonic wall and haustrum are clearly shown, but in absence of colonic lumen.

10. The system of claim 6, wherein when the computer program is executed, the processor is controlled to further perform a step of:
generating a marking for each of the assigned colonoscopy images, wherein the marking identifies the group to which the colonoscopy image is assigned.

11. A non-transitory computer-readable medium for evaluating colonoscopy performance, comprising a computer program stored therein, wherein when the computer program is executed, a device installing the non-transitory computer-readable medium is controlled to perform steps of:
(S1) splitting a video acquired during a colonoscopy examination into a plurality of colonoscopy images;
(S2) assigning each of the colonoscopy images into an inadequate-view group or an adequate-view group according to a first classification criterion, and assigning each colonoscopy image in the adequate-view group into a fold-inspection group or a lumen-inspection group according to a second classification criterion,
wherein the first classification criterion comprises at least one of clarity, exposure, level of tissue wrinkling, and level of occlusion in each of the colonoscopy images; the second classification criterion comprises at least one of an amount of haustrum, an amount of colonic lumen, and a position of the colonic lumen in each of the colonoscopy images, and
wherein the colonoscopy image in the adequate-view group is assigned into the fold-inspection group if the colonoscopy image meets one of the requirements of:
(R1) colonic wall is shown, but in absence of haustrum or colonic lumen;
(R2) colonic wall and haustrum are shown, but in absence of colonic lumen; and
(R3) colonic wall, haustrum and colonic lumen are shown, the amount of the haustrum shown falls within a range of 1 to 5, and the colonic lumen falls outside of a central area of the colonoscopy image; or the colonoscopy image in the adequate-view group is assigned into the lumen-inspection group if the colonoscopy image does not meet any of the requirements of (R1)-(R3); and (S3) determining a performance rating of the colonoscopy examination according to an elapsed time of at least one of the fold-inspection group, the lumen-inspection group, and the inadequate-view group.

12. The medium of claim 11, wherein the requirement of (R3) is defined as a center of the colonic lumen falling outside of the central area of the colonoscopy image, and the central area of the colonoscopy image is defined as a circular area centered at a center of the colonoscopy image and having a radius of 0.1-0.5 of a radius of the colonoscopy image.

13. The medium of claim 11, wherein the colonoscopy image is assigned into the inadequate-view group if the colonoscopy image meets one of the requirements of:
   (R4) a blurred area is shown and occupies more than half of a total area of the colonoscopy image;
   (R5) a reflection or a bubble is shown and occupies more than half of the total area of the colonoscopy image;
   (R6) fecal occlusion is shown and occupies more than half of the total area of the colonoscopy image; and
   (R7) wrinkled colonic wall is shown; or
   the colonoscopy image is assigned into the adequate-view group if the colonoscopy image does not meet any of the requirements of (R4)-(R7).

14. The medium of claim 13, wherein when the computer program is executed, the device installing the non-transitory computer-readable medium is controlled to further perform steps of:
   reassigning a colonoscopy image assigned to the inadequate-view group into the fold-inspection group if the colonoscopy image meets one of the requirements of:
      (R8) colonic wall is clearly shown, but in absence of haustrum or colonic lumen, and
      (R9) colonic wall and haustrum are clearly shown, but in absence of colonic lumen.

15. The medium of claim 11, when the computer program is executed, the device installing the non-transitory computer-readable medium is controlled to further perform a step of:
   generating a marking for each of the assigned colonoscopy images, wherein the marking identifies the group to which the colonoscopy image is assigned.

* * * * *